United States Patent
Tseng et al.

(10) Patent No.: US 11,324,790 B2
(45) Date of Patent: May 10, 2022

(54) METHOD FOR TREATING A TUBERCULOUS PROSTATITIS SIDE EFFECT CAUSED BY BCG PERFUSION THERAPY FOR BLADDER CANCER

(71) Applicant: Da-Tong Ju, Taipei (TW)

(72) Inventors: Hsuan-Ching Tseng, New Taipei (TW); Da-Tong Ju, Taipei (TW); Sung-Sen Yang, Taipei (TW); Wei-Te Cheng, New Taipei (TW); Chen-Yu Lee, Taipei (TW); Yan-Chih Liao, Taipei (TW); Juei-Yang Lo, New Taipei (TW); Luan-Yao Chien, Taipei (TW)

(73) Assignee: Da-Tong Ju, Taipei (TW)

( * ) Notice: Subject to any disclaimer, the term of this patent is extended or adjusted under 35 U.S.C. 154(b) by 0 days.

(21) Appl. No.: 16/995,903

(22) Filed: Aug. 18, 2020

(65) Prior Publication Data

US 2022/0054569 A1 Feb. 24, 2022

(51) Int. Cl.

| | |
|---|---|
| *A61K 36/282* | (2006.01) |
| *A61K 36/808* | (2006.01) |
| *A61K 36/40* | (2006.01) |
| *A61K 36/284* | (2006.01) |
| *A61K 36/756* | (2006.01) |
| *A61K 36/484* | (2006.01) |
| *A61K 36/21* | (2006.01) |
| *A61K 36/8945* | (2006.01) |
| *A61K 36/076* | (2006.01) |
| *A61K 36/65* | (2006.01) |
| *A61K 36/81* | (2006.01) |
| *A61K 36/31* | (2006.01) |
| *A61K 36/64* | (2006.01) |

(52) U.S. Cl.
CPC .......... *A61K 36/282* (2013.01); *A61K 36/076* (2013.01); *A61K 36/21* (2013.01); *A61K 36/284* (2013.01); *A61K 36/31* (2013.01); *A61K 36/40* (2013.01); *A61K 36/484* (2013.01); *A61K 36/64* (2013.01); *A61K 36/65* (2013.01); *A61K 36/756* (2013.01); *A61K 36/808* (2013.01); *A61K 36/81* (2013.01); *A61K 36/8945* (2013.01)

(58) Field of Classification Search
None
See application file for complete search history.

(56) References Cited

PUBLICATIONS

Penner, J., Zhi Bai Di Huang Wan, available at https://www.americandragon.com/Herb Formulas copy/ZhiBaiDiHuangWan.html, accessed on Sep. 30, 2021.*
Jun, X., et al., Pharmacological effects of medicinal components of Atractylodes lancea (Thunb.) DC., Chin Med (2018) 13:59 https://doi.org/10.1186/s13020-018-0216-7.*
Zeng Xuan-Jing, Zhu Da-Tong, Yang Song-Sheng, Cheng We-De, Lee Cheng-Yu, Liao Yan-Chih and Yu Da-Xiong, Case report on Chinese medicine medicinal treatment of a urethelial carcinoma patient with acute BCG-induced contact tuberculous prostatitis, JCMAS, vol. 7, No. 1, Dec. 2019, pp. 126-130.

* cited by examiner

*Primary Examiner* — H. Sarah Park
(74) *Attorney, Agent, or Firm* — Bacon & Thomas, PLLC

(57) ABSTRACT

A method for treating a side effect caused by bacillus Calmette-Guérin (BCG) perfusion therapy for bladder cancer includes: administering a Chinese medicine composition to a subject in need thereof; wherein, the Chinese medicine composition is an extract of a first mixture comprising *Rhizoma anemarrhenae, Cortex phellodendri, Glycyrrhiza uralensis, Rehmanniae Radix, Fructus corni, Rhizoma dioscoreae, Poria, Moutan cortex, Rhizoma Alismatis, Radix achyranthis bidentatae*, and *Atractylodes lancea*.

12 Claims, No Drawings

METHOD FOR TREATING A TUBERCULOUS PROSTATITIS SIDE EFFECT CAUSED BY BCG PERFUSION THERAPY FOR BLADDER CANCER

BACKGROUND OF THE INVENTION

1. Field of the Invention

The present invention relates to a method for treating a side effect caused by bacillus Calmette-Guérin (BCG) perfusion therapy for bladder cancer. More specifically, the present invention relates to a method for treating a tuberculous prostatitis side effect caused by bacillus Calmette-Guérin (BCG) perfusion therapy for bladder cancer.

2. Description of Related Art

According to the American Cancer Society, bladder cancer is the fourth most common cancer in men. Bladder cancer refers broadly to various malignant tumors from the bladder, including urothelial carcinoma, also known as transitional cell carcinoma (TCC), squamous cell carcinoma, adenocarcinoma, sarcoma, small cell carcinoma, and the like. Among them, urothelial carcinoma is the most common.

At present, surgery is mainly used to treat bladder cancer. The initial treatment is to scrape the tumor with endoscopic curettage, combined with chemotherapy drugs or bacille Calmette-Guérin (BCG) perfusion therapy to reduce the recurrence of bladder cancer. The BCG perfusion therapy destroy endothelial cells of the bladder using treated bacteria of BCG, thereby stimulating the patient's own immunity to eliminate tumor cells.

However, the bladder endometrium, prostate, urethral conjunctiva, and glans are all single-layered epithelium, which is easily penetrated by bacteria of BCG, causing side effects such as urinary tract infection, prostatitis, and balanitis. Therefore, there is a need to provide a treatment method to treat, alleviate or ameliorate the side effects induced by BCG perfusion therapy for bladder cancer.

SUMMARY OF THE INVENTION

In light of this, the present invention provides a Chinese medicine composition and treatment method that can treat, ameliorate or alleviate a side effect caused by bacillus Calmette-Guérin (BCG) perfusion therapy for bladder cancer.

One object of the present invention is to provide a Chinese medicine composition for treating a side effect caused by *bacillus* Calmette-Guérin (BCG) perfusion therapy for bladder cancer, wherein the Chinese medicine composition is an extract of a first mixture comprising *Rhizoma anemarrhenae, Cortex phellodendri, Glycyrrhiza uralensis, Rehmanniae Radix, Fructus corni, Rhizoma dioscoreae, Poria, Moutan cortex, Rhizoma Alismatis, Radix achyranthis bidentatae,* and *Atractylodes lancea.*

Another object of the present invention is to provide a method for treating a side effect caused by bacillus Calmette-Guérin (BCG) perfusion therapy for bladder cancer, comprising: administering said Chinese medicine composition to a subject in need thereof. Specifically, an effective amount of said Chinese medicine composition is administered to the subject in need thereof.

In the present invention, the first mixture may comprise 2-10 parts by weight of *Rhizoma anemarrhenae*, 1-5 parts by weight of *Cortex phellodendri*, 1-5 parts by weight of *Glycyrrhiza uralensis*, 6-10 parts by weight of *Rehmanniae Radix*, 2-6 parts by weight of *Fructus corni*, 2-6 parts by weight of *Rhizoma dioscoreae*, 2-6 parts by weight of *Poria*, 2-6 parts by weight of *Moutan cortex*, 2-10 parts by weight of *Rhizoma Alismatis*, 2-6 parts by weight of *Radix achyranthis bidentatae*, and 2-6 parts by weight of *Atractylodes lancea*. Preferably, the first mixture may comprise 3-9 parts by weight of *Rhizoma anemarrhenae*, 2-4 parts by weight of *Cortex phellodendri*, 2-4 parts by weight of *Glycyrrhiza uralensis*, 7-9 parts by weight of *Rehmanniae Radix*, 3-5 parts by weight of *Fructus corni*, 3-5 parts by weight of *Rhizoma dioscoreae*, 3-5 parts by weight of *Poria*, 3-5 parts by weight of *Moutan cortex*, 3-9 parts by weight of *Rhizoma Alismatis*, 3-5 parts by weight of *Radix achyranthis bidentatae*, and 3-5 parts by weight of *Atractylodes lancea*.

In one embodiment of the present invention, the first mixture may further comprise *Scrophulariae radix, Herba artemisiae annuae,* and *Cortex lycii*. Preferably, the first mixture may comprise 2-6 parts by weight of *Scrophulariae radix*, 1-5 parts by weight of *Herba artemisiae annuae*, and 2-6 parts by weight of *Cortex lycii*. More preferably, the first mixture may comprise 3-5 parts by weight of *Scrophulariae radix*, 2-4 parts by weight of *Herba artemisiae annuae*, and 3-5 parts by weight of *Cortex lycii*.

In one aspect of the present invention, the first mixture may comprise 6-10 parts by weight of *Rhizoma anemarrhenae*, 1-5 parts by weight of *Cortex phellodendri*, 1-5 parts by weight of *Glycyrrhiza uralensis*, 6-10 parts by weight of *Rehmanniae Radix*, 2-6 parts by weight of *Fructus corni*, 2-6 parts by weight of *Rhizoma dioscoreae*, 2-6 parts by weight of *Poria*, 2-6 parts by weight of *Moutan cortex*, 2-6 parts by weight of *Rhizoma Alismatis*, 2-6 parts by weight of *Radix achyranthis bidentatae*, 2-6 parts by weight of *Atractylodes lancea*, 2-6 parts by weight of *Scrophulariae radix*, 1-5 parts by weight of *Herba artemisiae annuae*, and 2-6 parts by weight of *Cortex lycii*. Preferably, the first mixture may comprise 7-9 parts by weight of *Rhizoma anemarrhenae*, 2-4 parts by weight of *Cortex phellodendri*, 2-4 parts by weight of *Glycyrrhiza uralensis*, 7-9 parts by weight of *Rehmanniae Radix*, 3-5 parts by weight of *Fructus corni*, 3-5 parts by weight of *Rhizoma dioscoreae*, 3-5 parts by weight of *Poria*, 3-5 parts by weight of *Moutan cortex*, 3-5 parts by weight of *Rhizoma Alismatis*, 3-5 parts by weight of *Radix achyranthis bidentatae*, 3-5 parts by weight of *Atractylodes lancea*, 3-5 parts by weight of *Scrophulariae radix*, 2-4 parts by weight of *Herba artemisiae annuae*, and 3-5 parts by weight of *Cortex lycii*.

In another embodiment, the first mixture may further comprise *Raphani semen*. Preferably, the first mixture may comprise 2-6 parts by weight of *Raphani semen*. More preferably, the first mixture may comprise 3-5 parts by weight of *Raphani semen*.

In yet another embodiment of the present invention, the first mixture may further comprise *Scrophulariae radix, Herba artemisiae annuae, Cortex lycii*, and *Raphani semen*. Preferably, the first mixture may comprise 6-10 parts by weight of *Rhizoma anemarrhenae*, 1-5 parts by weight of *Cortex phellodendri*, 1-5 parts by weight of *Glycyrrhiza uralensis*, 6-10 parts by weight of *Rehmanniae Radix*, 2-6 parts by weight of *Fructus corni*, 2-6 parts by weight of *Rhizoma dioscoreae*, 2-6 parts by weight of *Poria*, 6-10 parts by weight of *Rhizoma Alismatis*, 2-6 parts by weight of *Radix achyranthis bidentatae*, 2-6 parts by weight of *Atractylodes lancea*, 2-6 parts by weight of *Scrophulariae radix*, 1-5 parts by weight of *Herba artemisiae annuae*, 2-6 parts by weight of *Cortex*

*lycii*, and 2-6 parts by weight of *Raphani semen*. More preferably, the first mixture may comprise 7-9 parts by weight of *Rhizoma anemarrhenae*, 2-4 parts by weight of *Cortex phellodendri*, 2-4 parts by weight of *Glycyrrhiza uralensis*, 7-9 parts by weight of *Rehmanniae Radix*, 3-5 parts by weight of *Fructus corni*, 3-5 parts by weight of *Rhizoma dioscoreae*, 3-5 parts by weight of *Poria*, 3-5 parts by weight of *Moutan cortex*, 7-9 parts by weight of *Rhizoma Alismatis*, 3-5 parts by weight of *Radix achyranthis bidentatae*, 3-5 parts by weight of *Atractylodes lancea*, 3-5 parts by weight of *Scrophulariae radix*, 2-4 parts by weight of *Herba artemisiae annuae*, 3-5 parts by weight of *Cortex lycii*, and 3-5 parts by weight of *Raphani semen*.

The Chinese medicine composition of the present invention is prepared by the following steps: providing the first mixture; mixing the first mixture with water to form a second mixture; and heating the second mixture to obtain the Chinses medicine composition. In addition, a crude extract may be obtained after heating the second mixture; and, the Chinese medicine composition may be obtained by filtering the crude extract and retaining the liquid.

Here, in the present invention, the part by weight may be 2.5-5 gram per part. Preferably, the part by weight is 3-4 gram per part. More preferably, the part by weight is 3.75 gram per part.

In the present invention, said "bladder cancer" comprises urothelial carcinoma, squamous cell carcinoma, adenocarcinoma, sarcoma, or small cell carcinoma. However, the present invention is not limited thereto. Said "side effect" comprises prostatitis; more specifically, the prostatitis may be tuberculous prostatitis. However, the present invention is not limited thereto.

The present invention is not restrictive of the method for heating the Chinese medicine, and it can be implemented by any known method, such as direct heating and double-boiling.

In the present invention, the term "treat" or "treatment" used herein includes ameliorating, alleviating, or improving related symptoms, or inhibiting or controlling the progression of the disease. However, the present invention is not limited thereto.

In the present invention, the term "effective amount" used herein refers to a necessary dose leading to expected therapeutic effects in a subject treated, and it may be changed depending on the route of administration, the use of excipients and the combined use with other medicaments.

The Chinese medicine composition of the present invention may be administered via oral administration or injection.

The Chinese medicine composition of the present invention may further comprise pharmaceutically acceptable carrier, stabilizer, diluent, dispersant, suspending agents, thickening agent, excipient, or the combination thereof.

In the present invention, the term "acceptable" used herein refers to that it should be compatible with the Chinese medicine composition, preferably able to stabilize the Chinese medicine composition, and not jeopardize the subject treated.

The present invention achieve the object of treating a side effect caused by bacillus Calmette-Guérin (BCG) perfusion therapy for bladder cancer, by administering a specific Chinese medicine composition to a subject in need thereof.

DETAILED DESCRIPTION OF THE PREFERRED EMBODIMENT

The following embodiments are meant to explain the implementation of the present invention, they should be construed as descriptive merely, and should not restrict the remaining part of the present invention. The person having ordinary skills in the art can easily understand other advantages and effects of the present invention. The present invention may also be implemented or applied by other different embodiments, and various details in this specification may also be modified and changed according to different viewpoints and applications without departing from the spirit of the invention.

In addition, ordinal numbers such as "first", "second" and the like used in the specification and claim for modifying elements of the claim do not mean and represent the claimed elements have any antecedent ordinal number, nor do they represent the order (or order of production) between a claimed element and another claimed element. The ordinal numbers are only used to clearly distinguish certain claimed elements having the same name.

The preparation of the Chinese medicine composition of the present invention is described below, wherein the materials used in the present invention are commercially available and easily available. In addition, the part by weight by weight is 3.75 gram per part.

Preparation Example 1: Preparation of Chinese Medicine Composition-1

Provide 4 parts by weight of *Rhizoma anemarrhenae*, 3 parts by weight of *Cortex phellodendri*, 3 parts by weight of *Glycyrrhiza uralensis*, 8 parts by weight of *Rehmanniae Radix*, 4 parts by weight of *Fructus corni*, 4 parts by weight of *Rhizoma dioscoreae*, 4 parts by weight of *Poria*, 4 parts by weight of *Moutan cortex*, 4 parts by weight of *Rhizoma Alismatis*, 4 parts by weight of *Radix achyranthis bidentatae*, 4 parts by weight of *Atractylodes lancea*, 4 parts by weight of *Scrophulariae radix*, 3 parts by weight of *Herba artemisiae annuae*, and 4 parts by weight of *Cortex lycii* to form a first mixture-1; mix the first mixture-1 with about 267 parts by weight of water to form a second mixture-1; heat the second mixture-1 for about 1 hour to obtain about 107 parts by weight of a crude extract followed by filtering; and, obtain a Chinese medicine composition-1.

Preparation Example 2: Preparation of Chinese Medicine Composition-2

Provide 8 parts by weight of *Rhizoma anemarrhenae*, 3 parts by weight of *Cortex phellodendri*, 3 parts by weight of *Glycyrrhiza uralensis*, 8 parts by weight of *Rehmanniae Radix*, 4 parts by weight of *Fructus corni*, 4 parts by weight of *Rhizoma dioscoreae*, 4 parts by weight of *Poria*, 4 parts by weight of *Moutan cortex*, 4 parts by weight of *Rhizoma Alismatis*, 4 parts by weight of *Radix achyranthis bidentatae*, 4 parts by weight of *Atractylodes lancea*, 4 parts by weight of *Scrophulariae radix*, 3 parts by weight of *Herba artemisiae annuae*, and 4 parts by weight of *Cortex lycii* to form a first mixture-2; mix the first mixture-2 with about 267 parts by weight of water to form a second mixture-2; heat the second mixture-2 for about 1 hour to obtain about 107 parts by weight of a crude extract followed by filtering; and, obtain a Chinese medicine composition-2.

Preparation Example 3: Preparation of Chinese Medicine Composition-3

Provide 8 parts by weight of *Rhizoma anemarrhenae*, 3 parts by weight of *Cortex phellodendri*, 3 parts by weight of *Glycyrrhiza uralensis*, 8 parts by weight of *Rehmanniae*

*Radix*, 4 parts by weight of *Fructus corni*, 4 parts by weight of *Rhizoma dioscoreae*, 4 parts by weight of *Poria*, 4 parts by weight of *Moutan cortex*, 8 parts by weight of *Rhizoma Alismatis*, 4 parts by weight of *Radix achyranthis bidentatae*, 4 parts by weight of *Atractylodes lancea*, 4 parts by weight of *Scrophulariae radix*, 3 parts by weight of *Herba artemisiae annuae*, 4 parts by weight of *Cortex lycii* and 4 parts by weight of *Raphani semen* to form a first mixture-3; mix the first mixture-3 with about 267 parts by weight of water to form a second mixture-3; heat the second mixture-3 for about 1 hour to obtain about 107 parts by weight of a crude extract followed by filtering; and, obtain a Chinese medicine composition-3.

Example 1

Due to urothelial carcinoma, a male patient of Example 1 was performed with tumor curettage and BCG perfusion therapy, and the patient had symptoms including night sweats, hot flashes, and morning lethargy ever since.

A treatment applied to the patient of Example 1 was described below. From day 1, a daily dose of the Chinese medicine composition-1 was administered to the patient every day, wherein the daily dose of the Chinese medicine composition-1 was divided into aliquots for ter in die administration. During the period of the treatment, a transurethral prostate biopsy was collected from the patient, thereby confirming tuberculous prostatitis. After taking the Chinese medicine composition-1 for three weeks, the symptoms of night sweats and hot flashes were no longer observed, and the side effect induced by the BCG perfusion therapy for urothelial carcinoma was significantly ameliorated. The follow-up showed that there was no recurrence of urothelial carcinoma and tuberculous prostatitis.

Example 2

Due to bladder cancer, a 33-year-old male patient of Example 2 was performed with tumor curettage and BCG perfusion therapy, and the patient had symptoms including night sweats ever since. In addition, the blood test result of GOT/GPT of the patient was 50/80. Moreover, a transurethral prostate biopsy was collected from the patient, thereby confirming prostatitis.

A treatment applied to the patient of Example 2 was described below. A daily dose of the Chinese medicine composition-2 was administered to the patient every day, wherein the daily dose of the Chinese medicine composition-2 was divided into aliquots for ter in die administration. After taking the Chinese medicine composition-2 for three weeks, the symptoms of night sweats was no longer observed. After two months, the blood test result of GOT/GPT of the patient was 30/30, and it was back to normal. After follow-up for more than 20 years, no recurrence of bladder cancer or prostatitis was found.

Example 3

A patient of Example 3 was performed with BCG perfusion therapy after receiving the surgery of bladder cancer. In the early stage, symptoms including night sweats, body fatigue, and evening hot flashes occurred, and tuberculous prostatitis was confirmed by the prostate biopsy in the late stage. In addition, the BCG perfusion therapy was suspended after the rising of GOT/GPT.

A treatment applied to the patient of Example 3 was described below. After the BCG therapy was suspended, a daily dose of the Chinese medicine composition-3 was administered to the patient every day, wherein the daily dose of the Chinese medicine composition-3 was divided into aliquots for ter in die administration. The Chinese medicine composition-3 was solely used to treat bladder cancer and tuberculous prostatitis in the patient of Example 3 after the suspension of BCG perfusion therapy. Said treatment was performed for four months, and there was no oddness shown in the bladder cancer and prostate tracking.

Although the present invention has been explained in relation to its preferred embodiment, it is to be understood that many other possible modifications and variations can be made without departing from the spirit and scope of the invention as hereinafter claimed.

What is claimed is:

1. A method for treating a side effect caused by bacillus Calmette-Guérin (BCG) perfusion therapy for bladder cancer, comprising:
    administering a Chinese medicine composition to a subject in need thereof;
    wherein, the Chinese medicine composition is an extract of a first mixture consisting of 2-10 parts by weight of *Rhizoma anemarrhenae*, 1-5 parts by weight of *Cortex phellodendri*, 1-5 parts by weight of *Glycyrrhiza uralensis*, 6-10 parts by weight of *Rehmanniae Radix*, 2-6 parts by weight of *Fructus corni*, 2-6 parts by weight of *Rhizoma dioscoreae*, 2-6 parts by weight of *Poria*, 2-6 parts by weight of *Moutan cortex*, 2-10 parts by weight of *Rhizoma Alismatis*, 2-6 parts by weight of *Radix achyranthis bidentatae*, 2-6 parts by weight of *Atractylodes lancea*, 2-6 parts by weight of *Scrophulariae radix*, 1-5 parts by weight of *Herba artemisiae annuae*, and 2-6 parts by weight of *Cortex lycii*,
    wherein the Chinese medicine composition is prepared by the following steps:
    providing the first mixture;
    mixing the first mixture with water to form a second mixture; and
    heating the second mixture to obtain the Chinese medicine composition.

2. The method of claim 1, wherein the first mixture comprises 3-9 parts by weight of *Rhizoma anemarrhenae*, 2-4 parts by weight of *Cortex phellodendri*, 2-4 parts by weight of *Glycyrrhiza uralensis*, 7-9 parts by weight of *Rehmanniae Radix*, 3-5 parts by weight of *Fructus corni*, 3-5 parts by weight of *Rhizoma dioscoreae*, 3-5 parts by weight of *Poria*, 3-5 parts by weight of *Moutan cortex*, 3-9 parts by weight of *Rhizoma Alismatis*, 3-5 parts by weight of *Radix achyranthis bidentatae*, 3-5 parts by weight of *Atractylodes lancea*, 3-5 parts by weight of *Scrophulariae radix*, 2-4 parts by weight of *Herba artemisiae annuae*, and 3-5 parts by weight of *Cortex lycii*.

3. The method of claim 1, wherein the part by weight is 2.5-5 gram per part.

4. A method for treating a side effect caused by bacillus Calmette-Guérin (BCG) perfusion therapy for bladder cancer, comprising:
    administering a Chinese medicine composition to a subject in need thereof;
    wherein, the Chinese medicine composition is an extract of a first mixture comprising 6-10 parts by weight of *Rhizoma anemarrhenae*, 1-5 parts by weight of *Cortex phellodendri*, 1-5 parts by weight of *Glycyrrhiza uralensis*, 6-10 parts by weight of *Rehmanniae Radix*, 2-6 parts by weight of *Fructus corni*, 2-6 parts by weight of *Rhizoma dioscoreae*, 2-6 parts by weight of *Poria*, 2-6 parts by weight of *Moutan cortex*, 6-10 parts by weight of *Rhizoma Alismatis*, 2-6 parts by weight of *Radix achyranthis bidentatae*, 2-6 parts by weight of *Atractylodes lancea*, 2-6 parts by weight of *Scrophulariae radix*, 1-5 parts by weight of *Herba artemisiae annuae*, 2-6 parts by weight of *Cortex lycii*, and 2-6 parts by weight of *Raphani semen*;

wherein the Chinese medicine composition is prepared by the following steps:

providing the first mixture;

mixing the first mixture with water to form a second mixture; and heating the second mixture to obtain the Chinese medicine composition.

5. The method of claim 4, wherein the first mixture comprises 7-9 parts by weight of *Rhizoma anemarrhenae*, 2-4 parts by weight of *Cortex phellodendri*, 2-4 parts by weight of *Glycyrrhiza uralensis*, 7-9 parts by weight of *Rehmanniae Radix*, 3-5 parts by weight of *Fructus corni*, 3-5 parts by weight of *Rhizoma dioscoreae*, 3-5 parts by weight of *Poria*, 3-5 parts by weight of *Moutan cortex*, 7-9 parts by weight of *Rhizoma Alismatis*, 3-5 parts by weight of *Radix achyranthis bidentatae*, 3-5 parts by weight of *Atractylodes lancea*, 3-5 parts by weight of *Scrophulariae radix*, 2-4 parts by weight of *Herba artemisiae annuae*, 3-5 parts by weight of *Cortex lycii*, and 3-5 parts by weight of *Raphani semen*.

6. The method of claim 1, wherein the bladder cancer comprises urothelial carcinoma, squamous cell carcinoma, adenocarcinoma, sarcoma, or small cell carcinoma.

7. The method of claim 1, wherein the side effect comprises prostatitis.

8. The method of claim 7, wherein the prostatitis is tuberculous prostatitis.

9. The method of claim 4, wherein the part by weight is 2.5-5 gram per part.

10. The method of claim 4, wherein the bladder cancer comprises urothelial carcinoma, squamous cell carcinoma, adenocarcinoma, sarcoma, or small cell carcinoma.

11. The method of claim 4, wherein the side effect comprises prostatitis.

12. The method of claim 11, wherein the prostatitis is tuberculous prostatitis.

* * * * *